(12) United States Patent
Tateno et al.

(10) Patent No.: US 7,919,430 B2
(45) Date of Patent: Apr. 5, 2011

(54) CATALYST FOR OXIDATION OR AMMOXIDATION, AND PROCESS FOR PRODUCING THE SAME

(75) Inventors: Eri Tateno, Tokyo (JP); Satoru Komada, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 361 days.

(21) Appl. No.: 12/293,795

(22) PCT Filed: Mar. 15, 2007

(86) PCT No.: PCT/JP2007/055251
§ 371 (c)(1),
(2), (4) Date: Sep. 19, 2008

(87) PCT Pub. No.: WO2007/119376
PCT Pub. Date: Oct. 25, 2007

(65) Prior Publication Data
US 2010/0240921 A1    Sep. 23, 2010

(30) Foreign Application Priority Data

Mar. 20, 2006 (JP) ................................. 2006-077557

(51) Int. Cl.
*B01J 23/22* (2006.01)
*B01J 23/02* (2006.01)
*B01J 23/10* (2006.01)
*B01J 23/30* (2006.01)
*C07C 23/24* (2006.01)

(52) U.S. Cl. ........ 502/312; 502/241; 502/302; 502/304; 502/306; 558/308

(58) Field of Classification Search .................. None
See application file for complete search history.

(56) References Cited

U.S. PATENT DOCUMENTS

| | | | |
|---|---|---|---|
| 7,109,144 B2 * | 9/2006 | Hinago et al. | ................ 502/312 |
| 2002/0115879 A1 | 8/2002 | Hinago et al. | |
| 2003/0088118 A1 | 5/2003 | Komada et al. | |
| 2003/0187299 A1 | 10/2003 | Machhammer et al. | |
| 2004/0063988 A1 | 4/2004 | Hechler et al. | |
| 2004/0192966 A1 | 9/2004 | Hazin et al. | |

FOREIGN PATENT DOCUMENTS

| | | |
|---|---|---|
| CN | 1360971 A | 7/2002 |
| CN | 1443151 | 9/2003 |
| CN | 1701054 | 11/2005 |
| EP | 0 005 769 | 12/1979 |
| JP | 58-166939 | 10/1983 |
| JP | 7-315842 | 12/1995 |
| JP | 10-28862 | 2/1998 |
| JP | 11-253801 | 9/1999 |
| JP | 2000-126599 | 9/2000 |
| JP | 2001-206870 | 7/2001 |
| JP | 2002-177777 | 6/2002 |
| JP | 2002-239382 | 8/2002 |
| JP | 2004-66024 | 3/2004 |
| JP | 2004-148302 | 5/2004 |
| JP | 2005-211844 | 8/2005 |
| WO | WO 01/96016 A1 | 12/2001 |
| WO | WO 2005/089943 A1 | 9/2005 |

OTHER PUBLICATIONS

Office Action dated Jul. 27, 2010 issued in corresponding Chinese application.
Supplementary European Search Report dated Jan. 24, 2011 issued in corresponding International Application No. PCT/JP2007/055251.

* cited by examiner

*Primary Examiner* — Kamal A Saeed
(74) *Attorney, Agent, or Firm* — Finnegan, Henderson, Farabow, Garrett & Dunner, L.L.P.

(57) ABSTRACT

It is an object to provide a novel oxide catalyst for producing an unsaturated acid or unsaturated nitrile by which reaction results are good and a high yield can be stably maintained for a prolonged period of time, a process for producing the oxide catalyst, and a process for producing an unsaturated acid or unsaturated nitrile using the oxide catalyst. According to the present invention, there is provided an oxide catalyst represented by following compositional formula (1):

$$Mo_1V_aSb_bNb_cMn_dW_eY_fO_n \qquad (1)$$

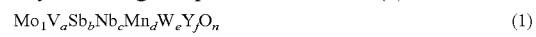

wherein Y represents at least one element selected from alkaline earth metals and rare earth metals; a, b, c, d, e, f, and n each represents an atomic ratio based on one atom of Mo; $0.1 \leq a \leq 1$, $0.01 \leq b \leq 1$, $0.01 \leq c \leq 1$, $0 \leq d \leq 0.1$, $0 \leq e \leq 0.1$, $0 < (d+e) \leq 0.1$, $0 \leq f \leq 1$; and n is a number determined by valencies of the constituent metals.

13 Claims, No Drawings

CATALYST FOR OXIDATION OR AMMOXIDATION, AND PROCESS FOR PRODUCING THE SAME

TECHNICAL FIELD

The present invention relates to an oxide catalyst for use in a vapor-phase catalytic oxidation or a vapor-phase catalytic ammoxidation of propane or isobutane, and a process for producing an unsaturated acid or unsaturated nitrile using the catalyst.

BACKGROUND ART

Processes for subjecting propylene or isobutlyene to the vapor-phase catalytic oxidation or the vapor-phase catalytic ammoxidation so as to produce the corresponding unsaturated carboxylic acid or unsaturated nitrile have been well known from hitherto. In recent years, processes for subjecting propane or isobutane instead of propylene or isobutlyene to the vapor-phase catalytic oxidation or the vapor-phase catalytic ammoxidation so as to produce the corresponding unsaturated carboxylic acid or unsaturated nitrile have attracted attention, and various catalysts and reaction processes have been proposed.

For example, oxide catalysts containing Mo—V—Nb—Sb or Mo—V—Nb—Te have been disclosed in Patent Document 1 (WO 01/096016), Patent Document 2 (Japanese Patent Application Laid-open No. 2004-148302), Patent Document 3 (Japanese Patent Application Laid-open No. 10-28862), Patent Document 4 (Japanese Patent Application Laid-open No. 2002-239382), Patent Document 5 (Japanese Patent Application Laid-open No. 11-253801), Patent Document 6 (Japanese Patent Application Laid-open No. 07-315842) and Patent Document 7 (Japanese Patent Application Laid-open No. 2001-206870). Of these patent documents, for example in Patent Document 1 (WO 01/096016), it is stated that a specified element (Al or W) for which the element and/or an oxide thereof forms a rutile-like structure may be contained in the Mo—V—Nb—Te or Mo—V—Nb—Sb. However, the main composition of oxide catalysts actually disclosed is Mo—V—Nb—Sb—Ti or Mo—V—Nb—Sb—Al, and the yield therefor is still insufficient.

Moreover, in Patent Document 2 (Japanese Patent Application Laid-open No. 2004-148302), there is described an example in which acrylic acid is obtained from propane using a catalyst obtained by subjecting a mixture of tellurium dioxide and ammonium heptamolybdate to hydrothermal treatment for 1.5 hours at 100° C., adding manganese (II) nitrate, vanadyl sulfate hydrate and ammonium niobium oxalate while stirring, and subjecting to hydrothermal treatment for 4 days at 175° C. However, a sufficient acrylic acid yield is still not exhibited. In addition, when preparing the catalyst, hydrothermal treatment for a prolonged period of time at a high temperature is required, and many steps including pressurization, filtration, washing and drying are required, and hence the operational process is complex, and thus there is a problem that industrialization is accompanied by difficulties.

When carrying out the vapor-phase catalytic oxidation/ammoxidation industrially, it is important to maintain a high yield for a prolonged period of time. In Patent Document 3 (Japanese Patent Application Laid-open No. 10-28862), there is disclosed an example in which W, a rare earth element, and an alkaline earth metal or the like are impregnated into a catalyst having a main composition of Mo—V—Nb—Te, whereby a high yield can be obtained. However, Te contained in the catalyst evaporates during reaction, and hence it is difficult to maintain a high yield over a prolonged period of time. Moreover, the yield for a Mo—V—Nb—Sb system is still low, and hence there is no disclosure regarding achieving both good yield and good lifetime simultaneously.

In the other patent documents, for example Patent Document 4 (Japanese Patent Application Laid-open No. 2002-239382), Patent Document 5 (Japanese Patent Application Laid-open No. 11-253801), Patent Document 6 (Japanese Patent Application Laid-open No. 07-315842) and Patent Document 7 (Japanese Patent Application Laid-open No. 2001-206870), use of manganese (Mn) or tungsten (W) is described, but the reaction results are still insufficient.

Patent Document 1: WO 01/096016
Patent Document 2: Japanese Patent Application Laid-open No. 2004-148302
Patent Document 3: Japanese Patent Application Laid-open No. 10-28862
Patent Document 4: Japanese Patent Application Laid-open No. 2002-239382)
Patent Document 5: Japanese Patent Application Laid-open No. 11-253801
Patent Document 6: Japanese Patent Application Laid-open No. 07-315842)
Patent Document 7: Japanese Patent Application Laid-open No. 2001-206870

DISCLOSURE OF INVENTION

Problems to be Solved by the Invention

It is an object of the present invention to provide a novel oxide catalyst for producing an unsaturated acid or unsaturated nitrile by which a high yield can be stably maintained for a prolonged period of time, a process for producing the oxide catalyst, and a process for producing an unsaturated acid or unsaturated nitrile using the oxide catalyst.

Means for Solving the Problems

The present inventors carried out assiduous studies into catalysts for use in the vapor-phase catalytic oxidation or vapor-phase catalytic ammoxidation of propane or isobutane, and as a result, completed the present invention upon discovering that the above object can be attained by using a catalyst containing Sb, Mo, V, Nb, and Mn and/or W in a suitable composition.

That is, in the first aspect of the present invention, there are provided:

[1] an oxide catalyst for use in a vapor-phase catalytic oxidation or a vapor-phase catalytic ammoxidation of propane or isobutane, the oxide catalyst represented by following compositional formula (1):

$$Mo_1V_aSb_bNb_cMn_dW_eY_fO_n \qquad (1)$$

wherein Y represents at least one element selected from alkaline earth metals and rare earth metals;

a, b, c, d, e, f, and n each represents an atomic ratio based on one atom of Mo;

$0.1 \leq a \leq 1$, $0.01 \leq b \leq 1$, $0.01 \leq c \leq 1$, $0 \leq d \leq 0.1$, $0 \leq e \leq 0.1$, $0 < (d+e) \leq 0.1$, $0 \leq f \leq 1$; and n is a number determined by valencies of the constituent metals,

[2] the oxide catalyst according to item [1], wherein in the compositional formula (1), e=0, and $0 < d \leq 0.08$,

[3] the oxide catalyst according to item [1], wherein in the compositional formula (1), d=0, and $0 < e \leq 0.08$,

[4] the oxide catalyst according to item [1], wherein in the compositional formula (1), 0<d, 0<e, and (d+e)≦0.08,
[5] the oxide catalyst according to any one of items [1] to [4], wherein in the compositional formula (1), Y is cerium, and f>0,
[6] the oxide catalyst according to any one of items [1] to [5], wherein the oxide catalyst is supported on silica, wherein a weight ratio of the silica is from 10 to 80 wt % in terms of $SiO_2$ based on the total weight of the silica and the oxide catalyst.

Further, in the second aspect of the present invention, there are provided:
[7] a process for producing the oxide catalyst according to any one of items [1] to [6], comprising;
  drying a mixture containing Mo, V, Sb, Nb, and Y (wherein Y represents at least one element selected from alkaline earth metals and rare earth metals), and Mn and/or W,
[8] a process for producing the oxide catalyst according to any one of items [1] to [6], comprising;
  mixing together a niobium-containing liquid having a dicarboxylic acid/niobium compound molar ratio of from 1 to 5, and a solution containing Mo, V and Sb,
[9] a process for producing the oxide catalyst according to any one of items [1] to [6], comprising the steps of;
  obtaining a catalyst precursor containing Mo, V, Sb and Nb; and
  immersing the catalyst precursor in a solution containing Mn and/or W,
[10] the process for producing the oxide catalyst according to item [9], wherein the catalyst precursor comprises Mn and/or W,
[11] the process for producing the oxide catalyst according to item [9] or [10], wherein the catalyst precursor comprises Y (wherein Y represents at least one element selected from alkaline earth metals and rare earth metals),
[12] the process for producing the oxide catalyst according to item [9] or [10], wherein the solution containing Mn and/or W has a pH of not more than 7.

Furthermore, in the third aspect of the present invention, there is provided:
[13] a process for producing an unsaturated acid or unsaturated nitrile by subjecting propane or isobutane to a vapor-phase catalytic oxidation or a vapor-phase catalytic ammoxidation, the process comprising bringing the propane or isobutane into contact with the oxide catalyst according to any one of items [1] to [6].

ADVANTAGEOUS EFFECTS OF THE INVENTION

By using the oxide catalyst according to the present invention in the vapor-phase catalytic oxidation or the vapor-phase catalytic ammoxidation of propane or isobutane, the vapor-phase catalytic oxidation or the vapor-phase catalytic ammoxidation can be made to proceed with high yield. Moreover, the oxide catalyst according to the present invention inherently has a long lifetime, and hence the vapor-phase catalytic oxidation or the vapor-phase catalytic ammoxidation can be carried out stably for a prolonged period of time.

BEST MODE FOR CARRYING OUT THE INVENTION

Following is a detailed description of the present invention.
An oxide catalyst according to the present invention is an oxide catalyst represented by following compositional formula (1):

$$Mo_1V_aSb_bNb_cMn_dW_eY_fO_n \quad (1)$$

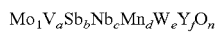

wherein Y represents at least one element selected from alkaline earth metals and rare earth metals; a, b, c, d, e, f, and n each represents an atomic ratio based on one atom of Mo; 0.1≦a≦1, 0.01≦b≦1, 0.01≦c≦1, 0≦d≦0.1, 0≦e≦0.1, 0<(d+e)≦0.1, 0≦f≦1; and n is a number determined by the valencies of the constituent metals.

The atomic ratios a to f based on one atom of Mo are respectively preferably in ranges of 0.1≦a≦0.5, 0.1≦b≦0.5, 0.01≦c≦0.5, 0≦d≦0.08, 0≦e≦0.08, and 0.001≦f≦0.2, more preferably 0.1≦a≦0.45, 0.1≦b≦0.45, 0.01≦c≦0.4, 0≦d≦0.05, 0≦e≦0.07, and 0.001≦f≦0.1. Note that the values of the atomic ratios a to f based on one atom of Mo indicate the compositional proportions of the constituent elements as charged in.

In one preferable aspect of the oxide catalyst according to the present invention, in above compositional formula (1), e=0, and 0<d≦0.08. More preferably 0<d≦0.06, yet more preferably 0<d≦0.04. Moreover, in another preferable aspect of the oxide catalyst according to the present invention, in above compositional formula (1), d=0, and 0<e≦0.08. More preferably 0<e≦0.07, yet more preferably 0<e≦0.05. Furthermore, in yet another preferable aspect of the oxide catalyst according to the present invention, in above compositional formula (1), 0<d, 0<e, and 0<(d+e)≦0.08. More preferably 0<(d+e)≦0.07, yet more preferably 0<(d+e)≦0.06.

The oxide catalyst according to the present invention is preferably a silica-supported catalyst. In the case that the oxide catalyst according to the present invention is a silica-supported catalyst, the oxide catalyst has high mechanical strength, and hence is suitable for ammoxidation using a fluidized bed reactor. The content of the silica carrier is preferably from 10 to 80 wt %, more preferably from 20 to 70 wt %, yet more preferably from 30 to 70 wt %, in terms of $SiO_2$ based on the total weight of the silica-supported oxide catalyst containing oxides of the elements constituting the catalyst and the silica carrier.

There are no particular limitations on the raw materials for the constituent metals for producing the oxide catalyst according to the present invention, but as raw materials for Mo and V, for example ammonium heptamolybdate (($NH_4)_6Mo_7O_{24}.4H_2O$) and ammonium metavanadate ($NH_4VO_3$) respectively can be suitably used. As a raw material for Nb, niobic acid, an inorganic acid salt of niobium, or an organic acid salt of niobium can be used, niobic acid being preferable. Niobic acid is represented by $Nb_2O_5.nH_2O$, and is also known as niobium hydroxide or niobium oxide hydrate. Furthermore, it is preferable to use the niobic acid in the form of a niobic acid-containing aqueous mixed liquid having a dicarboxylic acid/niobium molar ratio of from 1 to 5, preferably from 1.5 to 4.5, the dicarboxylic acid preferably being oxalic acid.

In the case that the catalyst contains Mn, manganese nitrate ($Mn(NO_3)_2.6H_2O$), manganese oxalate, manganese acetate, potassium permanganate or the like can be used as a raw material for Mn, manganese nitrate being particularly preferable. In the case that the catalyst contains W, ammonium metatungstate (($NH_4)_6(H_2W_{12}O_{40}).nH_2O$) is preferable as a raw material for W. An antimony oxide is suitable as a raw material for Sb, diantimony trioxide ($Sb_2O_3$) being particularly preferable. The component Y in above compositional formula (1) comprises at least one element selected from alkaline earth metals and rare earth metals, preferably a rare earth metal, particularly preferably Ce. As a raw material for component Y, an oxide or a nitrate can be used, a nitrate being preferable. As a raw material of the silica in the case that the catalyst is supported on a silica carrier, a silica sol can be suitably used, although powdered silica may also be used as some or all of the silica raw material. This powdered silica is preferably produced using a high temperature method. Furthermore, it is preferable to use the powdered silica dispersed in water.

Water is generally used as an aqueous medium for the raw material mixture, but to adjust the solubility of the raw material compounds in the aqueous medium, an alcohol may be used mixed into the water within a range such as not to have an adverse effect on the catalyst obtained. Examples of alcohols that can be used include alcohols having 1 to 4 carbon atoms.

In a process for producing the oxide catalyst according to the present invention, a mixed liquid containing the raw material compounds of the elements constituting compositional formula (1) are dried; otherwise there are no particular limitations, it being possible to prepare the oxide catalyst using an ordinary process. Here, in the present specification, the phrase "drying a mixture containing the elements constituting compositional formula (1)" means drying a mixture containing the raw material compounds so as to obtain a solid catalyst precursor. According to this production process, the catalyst precursor can be obtained simply by drying a solution or slurry containing the raw materials, and hence there is no need to precipitate out the solid by applying pressure to the solution or slurry or heating at a high temperature for a prolonged period of time as in the case of hydrothermal synthesis.

The first process for producing the oxide catalyst according to the present invention is a process comprising the three steps of (i-a) mixing together the raw materials, (ii) drying the raw material mixture obtained in step (i-a) so as to obtain a catalyst precursor, and (iii) calcining the catalyst precursor obtained in step (ii). Further, the second production process is a process comprising the steps of (i-b) drying a raw material mixture containing Mo, V, Sb, and Nb, and subsequently (iv) immersing the catalyst precursor obtained in a solution containing Mn and/or W. Furthermore, drying and calcination may be carried out after the immersion.

First Production Process
(Step i-a: Raw Material Mixing Step)

Ammonium heptamolybdate, ammonium metavanadate, and diantimony trioxide powders are added to water, and the mixture is heated to not less than 80° C. so as to prepare a mixed liquid (A). In the case of using a component Y, for example cerium nitrate, this may be added at the same time.

Niobic acid and oxalic acid are stirred together in water while heating so as to prepare a mixed liquid (B). The mixed liquid (B) is obtained through the following process. That is, niobic acid and oxalic acid are added to water, and the mixture is stirred so as to obtain a preliminary niobium aqueous solution or preliminary niobium aqueous suspension. In the case of a suspension, dissolution of the niobium compound can be promoted by adding a small amount of ammonia water or heating. Here, an amount used of the dicarboxylic acid is preferably made to be such that the molar ratio of the dicarboxylic acid to the niobium compound in terms of niobium is approximately from 3 to 6. If the amount used of the dicarboxylic acid is too high, then the niobium compound dissolves sufficiently, but when the preliminary niobium-containing aqueous solution or aqueous suspension obtained is cooled, a large amount of excess dicarboxylic acid precipitates out. As a result, of the dicarboxylic acid added, the amount actually used is reduced. On the other hand, if the amount used of the dicarboxylic acid is too low, then the niobium compound does not dissolve sufficiently, and hence, of the niobium compound added, the amount actually used is reduced. Moreover, in the case of heating, the heating temperature is generally from 50 to 100° C., preferably from 70 to 99° C., more preferably from 80 to 98° C. The concentration of the niobium compound (in terms of niobium) in the above preliminary niobium aqueous solution or preliminary niobium aqueous suspension is preferably made to be approximately from 0.2 to 0.8 mol-Nb/kg-liquid. Next, the aqueous solution or aqueous suspension is cooled, and solid is removed therefrom, thus obtaining a niobium stock liquid. The cooling can be carried out simply with ice, and the removal of solid can be carried out simply by decantation or filtration. Oxalic acid is added as appropriate to the niobium stock liquid obtained, whereby a suitable oxalic acid/niobium ratio can be obtained. The oxalic acid/niobium ratio molar ratio is preferably from 2 to 5, particularly preferably from 2 to 4. Furthermore, hydrogen peroxide may be added to the niobium mixed liquid ($B_0$) obtained, thus preparing the mixed liquid (B). In this case, the hydrogen peroxide/niobium molar ratio is preferably from 0.5 to 20, particularly preferably from 1 to 10.

The mixed liquid (A) and the mixed liquid (B) are suitably mixed together in accordance with the desired composition, thus obtaining a raw material mixture. In the case that the compositional formula (1) contains Mn and/or W, compound(s) containing Mn and/or W is/are mixed in as appropriate when obtaining the raw material mixture. As such a compound containing Mn or W, in general there can be used a nitrate, a carboxylic acid salt, a carboxylic acid ammonium salt, an oxalate, a peroxocarboxylic acid ammonium salt, or the like. Manganese nitrate and/or ammonium metatungstate is/are preferably used. The Mn-containing compound and/or W-containing compound may be added to the mixed liquid (A), or may be added in separately to the mixed liquid (B) and the mixed liquid (A) when mixing the mixed liquid (B) and the mixed liquid (A) together. In the case that the oxidation or ammoxidation catalyst according to the present invention is a silica-supported catalyst, the raw material mixture can be prepared containing a silica sol, the silica sol being added as appropriate.

Moreover, it is preferable to add hydrogen peroxide to the mixed liquid (A), or to a liquid containing a component of the mixed liquid (A) during the preparation of the mixed liquid (A). Here, the $H_2O_2$/Sb molar ratio is preferably from 0.01 to 5, particularly preferably from 0.05 to 4. Moreover, it is preferable to carry out stirring continuously for 30 minutes to 2 hours at 30 to 70° C. The raw material mixture obtained in this way may be a homogeneous solution, but is generally a slurry.

(Step ii: Drying Step)

The mixture obtained in the raw material mixing step is dried using a spray drying method, thus obtaining a dry powder. The spraying in the spray drying may be carried out using a centrifugal method, a two-fluid nozzle method, or a high-pressure nozzle method. As a heat source for the drying, steam, or air heated by an electric heater or the like may be used. The hot air drier inlet temperature is preferably from 150 to 300° C. The dry powder obtained is generally fed into the subsequent calcination step immediately. In the case that the dry powder must be stored, the dry powder is preferably stored such that there is no absorption of moisture.

(Step iii: Calcination Step)

The dry powder obtained through the drying step is calcined so as to obtain the oxide catalyst. The calcination is carried out under a vacuum or under an atmosphere of an inert gas substantially not containing oxygen such as nitrogen gas, argon gas or helium gas, preferably under an inert gas stream. On the other hand, an oxidizing component or reducing component may be added to the calcination atmosphere. The calcination step may be divided into pre-stage calcination and main calcination. The term "main calcination" means a stage in the calcination process for obtaining the catalyst in which the highest temperature is maintained, whereas the term "pre-stage calcination" means a calcination stage therebefore. In the pre-stage calcination, the temperature is preferably first held at from 250 to 450° C., preferably from 300 to 400° C., under an inert gas stream. The holding time is not less than 30 minutes, preferably from 3 to 8 hours. The pre-stage calcination may be further divided into a plurality of stages. In the case that the calcination is carried out using a batch system, the amount of the inert gas fed in is not less than 50 N-liter/hr, preferably from 50 to 5000 N-liter/hr, more preferably from 50 to 3000 N-liter/hr, based on 1 kg of the dry catalyst precursor (The term "N-liter" means a liter when measured under standard temperature and pressure conditions, i.e. 0° C. and 1 atmosphere).

In the case that the calcination is carried out using a continuous system, the amount of the inert gas fed in is not less than 50 N-liter, preferably from 50 to 5000 N-liter, more preferably from 50 to 3000 N-liter, based on 1 kg of the dry catalyst precursor. In the case of continuous flow calcination, air may get into the dry powder fed into the calcining tube, but if an inert gas counterflow is used, then there is no problem. When recovering the powder from the calcining apparatus after the pre-stage calcination, the powder is preferably recovered such as to not come into contact with air. The main calcination is carried out in the absence of oxygen, preferably at from 500 to 800° C., more preferably from 550 to 720° C. The calcination time is from 0.5 to 40 hours, preferably from 1 to 30 hours.

The calcination can be carried out using a rotary kiln, a tunnel kiln, a tube furnace, a fluidized calcining furnace, or the like. The calcination can be carried out repeatedly. In particular, a rotary kiln or a fluidized calcining furnace can be suitably used. If the dry catalyst precursor is calcined while being left sitting as is, then it is difficult to make the calcination uniform, and hence cracking or the like is prone to occur.

Second production process
(Step i-b: Raw Material Mixing Step, Step ii: Drying Step, Step iii: Calcination Step)

The raw material mixing step i-b in the second production process may be the same as the raw material mixing step i-a in the first production process, except that the raw material mixture need not contain Mn and/or W.

Moreover, drying step ii for the raw material mixture and the calcination step iii may be the same as in the first production process.

(Step iv: Immersion Step)

After the calcination, the catalyst is immersed in a solution containing Mn and/or W. In the case that the raw material mixture does not contain Mn in the raw material mixing step i-b described above, it is preferable for the catalyst precursor to be immersed in an Mn-containing solution in the immersion step iv. On the other hand, in the case that the raw material mixture does not contain W, it is preferable for the catalyst precursor to be immersed in a W-containing solution in the immersion step iv. In the case that the raw material mixture contains neither Mn nor W, it is preferable for the catalyst precursor to be immersed in a solution containing Mn and/or W in the immersion step iv.

The term "immersion" in the present specification means a state of placing the catalyst or catalyst precursor in a solution. The solution in which the catalyst or catalyst precursor has been placed is preferably stirred for not less than 1 minute. Moreover, the solution is preferably subjected to pressure reduction to below atmospheric pressure. The pressure may be reduced after the solution has been stirred for approximately 1 minute, or the pressure may be reduced during the stirring. It is thought that through such pressure reduction, pores in the catalyst are deaerated, and hence it becomes easier for the immersion solution to enter therein. The time for which the pressure is reduced is preferably from 2 to 60 minutes.

In the case of using the second production process, it is thought that the raw material mixture Mn and/or W can be localized on the surface of the catalyst.

The pH of the solution may be adjusted as appropriate. To adjust the pH, a generally used acid or alkali can be used. There are no particular limitations on the type of the acid/alkali, but in the case of making more acidic, nitric acid is preferable. The pH of the solution is preferably pH$\leq$6, more preferably 0$\leq$pH$\leq$4, particularly preferably 0$\leq$pH$\leq$3.

After the immersion, the solution is subjected to filtration or evaporation so as to recover the catalyst, which is then dried. There are no particular limitations on the drying process, which may be an ordinarily carried out process, although this process is preferably carried out for not less than 20 minutes at from 30 to 120° C. After the drying, calcination may again be carried out at a suitable temperature under an atmosphere of an interface such as nitrogen gas, or air or oxygen. The calcination is preferably carried out under an inert atmosphere for from 0.5 to 30 hours, more preferably from 1 to 20 hours, at from 200 to 750° C., more preferably from 250 to 690° C.

Propane or isobutane can be subjected to the vapor-phase catalytic oxidation or the vapor-phase catalytic ammoxidation under the presence of the oxide catalyst so as to produce the corresponding unsaturated acid or unsaturated nitrile. Preferably, propane or isobutane is subjected to the vapor-phase catalytic ammoxidation so as to produce the unsaturated nitrile. The catalyst may be used as is after having been calcined, or may be used after having been calcined and then subjected to immersion.

The raw materials fed in, i.e. propane or isobutane and ammonia, need not be of high purity, but rather industrial grade gases may be used. As an oxygen source fed in, air, oxygen-rich air, or pure oxygen may be used. Furthermore, helium, argon, carbon dioxide, steam, nitrogen gas or the like may be fed in as a diluent gas.

The molar ratio of the ammonia fed into the reaction to the alkane is from 0.3 to 1.5, preferably from 0.6 to 1.2. The molar ratio of the oxygen fed into the reaction to the alkane is from 0.1 to 6, preferably from 0.1 to 4. The reaction pressure is from 0.5 to 5 atm, preferably from 1 to 3 atm. The reaction temperature is from 350 to 550° C., preferably from 380 to 500° C.

The vapor-phase catalytic oxidation of propane or isobutane can be carried out under the following conditions. The raw materials fed in, i.e. propane or isobutane, need not be of high purity, but rather industrial grade gases may be used.

As an oxygen source fed in, air, pure oxygen, or oxygen-rich air may be used. Furthermore, helium, neon, argon, carbon dioxide, steam, nitrogen gas or the like may be fed in as a diluent gas.

In the case of ammoxidation, the molar ratio of the ammonia fed into the reaction system to the propane or isobutane is from 0.3 to 1.5, preferably from 0.8 to 1.2.

For either oxidation or ammoxidation, the molar ratio of molecular oxygen fed into the reaction system to the propane or isobutane is from 0.1 to 6, preferably from 0.1 to 4.

For either oxidation or ammoxidation, the reaction pressure is from 0.5 to 5 atm, preferably from 1 to 3 atm.

For either oxidation or ammoxidation, the reaction temperature is from 350 to 500° C., preferably from 380 to 470° C.

For either oxidation or ammoxidation, the contact time is from 0.1 to 10 sec·g/cc, preferably from 0.5 to 5 sec·g/cc. The contact time is defined by the following formula:

Contact Time(sec·g/cc)=$W/F \times 273/(273+T)$ wherein W=amount of catalyst packed in (g), F=raw material mixed gas flow rate (Ncc/sec) in standard state (0° C., 1.13× $10^5$ Pa), T=reaction temperature (° C.).

As the reaction system, a conventional type such as fixed bed, fluidized bed, or moving bed can be used, but a fluidized bed reactor for which heat of reaction can be easily removed is preferable. Moreover, the reaction of the present invention may be of one pass type or recycling type.

EXAMPLES

Following is the description of the oxide catalyst according to the present invention, giving examples of preparing the catalyst, examples of producing acrylonitrile through vapor-phase catalytic ammoxidation of propane, and examples of producing acrylic acid through vapor-phase catalytic oxidation of propane.

The results of the propane ammoxidation and/or oxidation were evaluated based on the results of analyzing the reaction gas, using as indicators the propane conversion and the acrylonitrile and/or acrylic acid selectivity, defined as in the formula formulae:

Propane conversion(%)=(no. mols propane reacted)/
(no. mols propane fed in)×100

Acrylonitrile(acrylic acid)selectivity(%)=(no. mols
acrylonitrile(acrylic acid)produced)/(no. mols
propane reacted)×100.

(Preparation of Niobium Stock Liquid)

A niobium stock liquid was prepared through the following process. 860 g of niobic acid having a $Nb_2O_5$ content of 80.2 wt %, and 3270 g of oxalic acid dihydrate ($H_2C_2O_4 \cdot 2H_2O$) were mixed into 5630 g of water. The oxalic acid/niobium molar ratio as charged in was 5.0, and the niobium concentration as charged in was 0.53 mol-Nb/kg-liquid. The resulting mixed liquid was stirred with heating for 1 hour at 95° C., thus obtaining an aqueous solution having niobium dissolved therein. The aqueous solution was left to stand and cooled with an ice, and then solid was filtered off by suction filtration, thus obtaining a homogeneous niobium-containing liquid. The oxalic acid/niobium molar ratio of the niobium-containing liquid was 2.28 according to the following analysis.

10 g of the niobium-containing liquid was accurately weighed out into a crucible, and after drying overnight at 95° C., heat treatment was carried out at 600° C. for 1 hour, thus obtaining 0.8912 g of $Nb_2O_5$. From this result, the niobium concentration was 0.6706 mol-Nb/kg-liquid. Moreover, 3 g of the niobium-containing liquid was accurately weighed out into a 300 ml glass beaker, 200 ml of hot water at approximately 80° C. was added, and then 10 ml of 1:1 sulfuric acid was added. While keeping the solution obtained at a temperature of 70° C. on a hot stirrer, titration was carried out using ¼ N $KMnO_4$ under stirring. The point at which a faint pink color due to the $KMnO_4$ remained for not less than approximately 30 seconds was taken as the end point. The oxalic acid concentration was calculated from the titration amount in accordance with the following formula, the result being 1.527 mol-oxalic acid/kg.

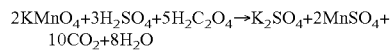

The niobium-containing liquid obtained was used as a niobium stock liquid in the following catalyst preparations without adjusting the oxalic acid/niobium molar ratio.

Example 1

Preparation of Catalyst

An oxide catalyst having a compositional formula as charged in represented by $Mo_1V_{0.25}Sb_{0.28}Nb_{0.085}Mn_{0.0025}W_{0.01}Ce_{0.01}O_n$/42 wt %-$SiO_2$ was prepared as follows. 300.6 g of ammonium heptamolybdate (($NH_4)_6Mo_7O_{24} \cdot 4H_2O$), 49.5 g of ammonium metavanadate ($NH_4VO_3$), 69.4 g of diantimony trioxide ($Sb_2O_3$), and 7.94 g of cerium nitrate ($Ce(NO_3)_3 \cdot 6H_2O$) were added to 1485 g of water, heating was carried out for 1 hour 30 minutes at 90° C. while stirring, and then cooling was carried out to approximately 70° C., thus obtaining a mixed liquid A-1. 621.2 g of a silica sol having a $SiO_2$ content of 29.3 wt % was added to the mixed liquid A-1 obtained. 80.5 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 15.9 g of oxalic acid and 32.6 g of a hydrogen peroxide aqueous solution having a $H_2O_2$ content of 30 wt % in 214.4 g of the niobium stock liquid prepared above, 1.22 g of manganese nitrate ($Mn(NO_3)_2 \cdot 6H_2O$), 7.84 g of ammonium metatungstate having a $WO_3$ content of 50 wt %, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under an 800 Ncc/min nitrogen gas stream, whereby a catalyst was obtained.

Ammoxidation of Propane:

35 g of the catalyst obtained in the "Preparation of catalyst" step of Example 1 was packed into a Vycor glass fluidized bed reaction tube having an inside diameter of 25 mm, and a mixed gas containing propane, ammonia, oxygen, and helium in a molar ratio of 1:0.8:2.8:15 was fed in with a contact time of 2.8 sec·g/cc under a reaction temperature of 440° C. and a reaction pressure of atmospheric pressure. The results after a reaction time of 5 hours are shown in Table 1, and the results after reaction times of 1200 and 3600 hours are shown in Table 2.

Example 2

Preparation of Catalyst

An oxide catalyst having a compositional formula as charged in represented by $Mo_1V_{0.25}Sb_{0.28}Nb_{0.085}Mn_{0.003}Ce_{0.01}O_n$/42 wt %-$SiO_2$ was prepared as follows. 303.8 g of ammonium heptamolybdate (($NH_4)_6Mo_7O_{24} \cdot 4H_2O$), 50.0 g of ammonium metavanadate ($NH_4VO_3$), 70.1 g of diantimony trioxide ($Sb_2O_3$) and 7.57 g of cerium nitrate ($Ce(NO_3)_3 \cdot 6H_2O$) were added to 1500 g of water, heating was carried out for 1 hour 30 minutes at 90° C. while stirring, and then cooling was carried out to approximately 70° C., thus obtaining a mixed liquid A-2. 621.2 g of a silica sol having a $SiO_2$ content of 29.3 wt % was added to the mixed liquid A-2 obtained. 81.4 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 16.1 g of oxalic acid and 32.9 g of a hydrogen peroxide aqueous solution having a $H_2O_2$ content of 30 wt % in 216.6 g of the niobium stock liquid prepared above, 1.47 g of manganese nitrate $(Mn(NO_3)_2 \cdot 6H_2O)$, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under an 800 Ncc/min nitrogen gas stream, whereby a catalyst was obtained.

(Ammoxidation of Propane)

Ammoxidation was carried out using the same process as in Example 1, but using the catalyst obtained in Example 2. The results after a reaction time of 5 hours are shown in Table 1, and the results after reaction times of 1200 and 3600 hours are shown in Table 2.

Example 3

Preparation of Catalyst

An oxide catalyst having a compositional formula as charged in represented by $Mo_1V_{0.25}Sb_{0.28}Nb_{0.085}W_{0.03}Ce_{0.01}O_n/42$ wt %-$SiO_2$ was prepared as follows. 294.8 g of ammonium heptamolybdate $((NH_4)_6Mo_7O_{24} \cdot 4H_2O)$, 48.5 g of ammonium metavanadate $(NH_4VO_3)$, 68.0 g of diantimony trioxide $(Sb_2O_3)$, and 7.35 g of cerium nitrate $(Ce(NO_3)_3 \cdot 6H_2O)$ were added to 1455 g of water, heating was carried out for 1 hour 30 minutes at 90° C. while stirring, and then cooling was carried out to approximately 70° C., thus obtaining a mixed liquid A-3. 621.2 g of a silica sol having a $SiO_2$ content of 29.3 wt % was added to the mixed liquid A-3 obtained. 79.0 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 15.6 g of oxalic acid and 32.0 g of a hydrogen peroxide aqueous solution having a $H_2O_2$ content of 30 wt % in 210.2 g of the niobium stock liquid prepared above, 23.1 g of ammonium metatungstate having a $WO_3$ content of 50 wt %, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained.

(Ammoxidation of Propane)

Ammoxidation was carried out using the same process as in Example 1, but using the catalyst obtained in Example 3. The results after a reaction time of 5 hours are shown in Table 1, and the results after reaction times of 1200 and 3600 hours are shown in Table 2.

Example 4

Preparation of Catalyst

An oxide catalyst having a compositional formula as charged in represented by $Mo_1V_{0.25}Sb_{0.28}Nb_{0.085}Mn_{0.004}W_{0.01}O_n/42$ wt %-$SiO_2$ was prepared as follows. 302.8 g of ammonium heptamolybdate $((NH_4)_6Mo_7O_{24} \cdot 4H_2O)$, 49.8 g of ammonium metavanadate $(NH_4VO_3)$, and 69.8 g of diantimony trioxide $(Sb_2O_3)$ were added to 1500 g of water, heating was carried out for 1 hour 30 minutes at 90° C. while stirring, and then cooling was carried out to approximately 70° C., thus obtaining a mixed liquid A-4. 621.2 g of a silica sol having a $SiO_2$ content of 29.3 wt % was added to the mixed liquid A-4 obtained. 81.1 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 16.0 g of oxalic acid and 32.8 g of a hydrogen peroxide aqueous solution having a $H_2O_2$ content of 30 wt % in 215.9 g of the niobium stock liquid prepared above, 7.90 g of ammonium metatungstate having a $WO_3$ content of 50 wt %, 1.96 g of manganese nitrate, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained.

(Ammoxidation of Propane)

Ammoxidation was carried out using the same process as in Example 1, but using the catalyst obtained in Example 4. The results after a reaction time of 5 hours are shown in Table 1, and the results after reaction times of 1200 and 3600 hours are shown in Table 2.

Comparative Example 1

Preparation of Catalyst

An oxide catalyst having a compositional formula as charged in represented by $Mo_1V_{0.25}Sb_{0.28}Nb_{0.085}Ce_{0.01}O_n/42$ wt %-$SiO_2$ was prepared as follows. 304.1 g of ammonium heptamolybdate $((NH_4)_6Mo_7O_{24} \cdot 4H_2O)$, 50.0 g of ammonium metavanadate $(NH_4VO_3)$, 70.1 g of diantimony trioxide $(Sb_2O_3)$, and 7.58 g of cerium nitrate $(Ce(NO_3)_3 \cdot 6H_2O)$ were added to 1501 g of water, heating was carried out for 1 hour 30 minutes at 90° C. while stirring, and then cooling was carried out to approximately 70° C., thus obtaining a mixed liquid A-5. 621.2 g of a silica sol having a $SiO_2$ content of 29.3 wt % was added to the mixed liquid A-5 obtained. 81.5 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 16.1 g of oxalic acid and 33.0 g of a hydrogen peroxide aqueous solution having a $H_2O_2$ content of 30 wt % in 216.8 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained.

(Ammoxidation of Propane)

Ammoxidation was carried out using the same process as in Example 1, but using the catalyst obtained in Comparative Example 1. The results after a reaction time of 5 hours are shown in Table 1, and the results after reaction times of 1200 and 3600 hours are shown in Table 2.

Comparative Example 2

Preparation of Catalyst

An oxide catalyst having a compositional formula as charged in represented by $Mo_1V_{0.25}Sb_{0.28}Nb_{0.085}Mn_{0.2}O_n$/42 wt %-$SiO_2$ was prepared as follows. 287.7 g of ammonium heptamolybdate (($NH_4$)$_6Mo_7O_{24}$.$4H_2O$), 47.3 g of ammonium metavanadate ($NH_4VO_3$), and 66.4 g of diantimony trioxide ($Sb_2O_3$) were added to 1420 g of water, heating was carried out for 1 hour 30 minutes at 90° C. while stirring, and then cooling was carried out to approximately 70° C., thus obtaining a mixed liquid A-6. 621.2 g of a silica sol having a $SiO_2$ content of 29.3 wt % was added to the mixed liquid A-6 obtained. 77.1 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 15.2 g of oxalic acid and 31.2 g of a hydrogen peroxide aqueous solution having a $H_2O_2$ content of 30 wt % in 205.1 g of the niobium stock liquid prepared above, 93.0 g of manganese nitrate ($Mn(NO_3)_2$.$6H_2O$), and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained.

(Ammoxidation of Propane)

Ammoxidation was carried out using the same process as in Example 1, but using the catalyst obtained in Comparative Example 2. The results after a reaction time of 5 hours are shown in Table 1, and the results after reaction times of 1200 and 3600 hours are shown in Table 2.

Comparative Example 3

Preparation of Catalyst

An oxide catalyst having a compositional formula as charged in represented by $Mo_1V_{0.25}Sb_{0.28}Nb_{0.085}W_{0.2}Ce_{0.01}O_n$/42 wt %-$SiO_2$ was prepared as follows. 251.2 g of ammonium heptamolybdate (($NH_4$)$_6Mo_7O_{24}$.$4H_2O$), 41.3 g of ammonium metavanadate ($NH_4VO_3$), 58.0 g of diantimony trioxide ($Sb_2O_3$), and 6.26 g of cerium nitrate ($Ce(NO_3)_3$.$6H_2O$) were added to 1240 g of water, heating was carried out for 1 hour 30 minutes at 90° C. while stirring, and then cooling was carried out to approximately 70° C., thus obtaining a mixed liquid A-7. 621.2 g of a silica sol having a $SiO_2$ content of 29.3 wt % was added to the mixed liquid A-7 obtained. 67.3 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 13.3 g of oxalic acid and 27.2 g of a hydrogen peroxide aqueous solution having a $H_2O_2$ content of 30 wt % in 179.1 g of the niobium stock liquid prepared above, 131.1 g of ammonium metatungstate having a $WO_3$ content of 50 wt %, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained.

(Ammoxidation of Propane)

Ammoxidation was carried out using the same process as in Example 1, but using the catalyst obtained in Comparative Example 3. The results after a reaction time of 5 hours are shown in Table 1, and the results after reaction times of 1200 and 3600 hours are shown in Table 2.

Comparative Example 4

Preparation of Catalyst

An oxide catalyst having a compositional formula as charged in represented by $Mo_1V_{0.24}Sb_{0.28}Nb_{0.085}Mn_{0.08}W_{0.08}Ce_{0.01}O_n$/42 wt %-$SiO_2$ was prepared as follows. 274.0 g of ammonium heptamolybdate (($NH_4$)$_6Mo_7O_{24}$.$4H_2O$), 45.1 g of ammonium metavanadate ($NH_4VO_3$), 63.2 g of diantimony trioxide ($Sb_2O_3$), and 6.83 g of cerium nitrate ($Ce(NO_3)_3$.$6H_2O$) were added to 1353 g of water, heating was carried out for 1 hour 30 minutes at 90° C. while stirring, and then cooling was carried out to approximately 70° C., thus obtaining a mixed liquid A-8. 621.2 g of a silica sol having a $SiO_2$ content of 29.3 wt % was added to the mixed liquid A-8 obtained. 73.4 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 29.7 g of a hydrogen peroxide aqueous solution having a $H_2O_2$ content of 30 wt % in 195.3 g of the niobium stock liquid prepared above, 57.2 g of ammonium metatungstate having a $WO_3$ content of 50 wt %, 35.4 g of manganese nitrate ($Mn(NO_3)_2$.$6H_2O$), and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained.

(Ammoxidation of Propane)

Ammoxidation was carried out using the same process as in Example 1, but using the catalyst obtained in Comparative Example 4. The results after a reaction time of 5 hours are shown in Table 1, and the results after reaction times of 1200 and 3600 hours are shown in Table 2.

Comparative Example 5

Preparation of Catalyst

An oxide catalyst having a compositional formula as charged in represented by $Mo_1V_{0.21}Sb_{0.25}Nb_{0.09}Ce_{0.005}O_n/45M\%$-$SiO_2$ was prepared as follows. 304.3 g of ammonium heptamolybdate $((NH_4)_6Mo_7O_{24}.4H_2O)$, 50.1 g of ammonium metavanadate $(NH_4VO_3)$, 70.2 g of diantimony trioxide $(Sb_2O_3)$, and 3.79 g of cerium nitrate $(Ce(NO_3)_3.6H_2O)$ were added to 1502 g of water, heating was carried out for 1 hour 30 minutes at 90° C. while stirring, and then cooling was carried out to approximately 70° C., thus obtaining a mixed liquid A-9. 665.5 g of a silica sol having a $SiO_2$ content of 29.3 wt % was added to the mixed liquid A-9 obtained. 81.5 g of a hydrogen peroxide aqueous solution having a $H_2O_2$ content of 30 wt % was further added, and stirring was continued for 1 hour at 52° C. In a separate vessel, 97.5 g of powdered silica was dispersed in 1270 g of water, and the mixture was stirred for at least 3 hours at room temperature so as to prepare a powdered silica dispersion. Next, a mixture of 34.9 g of a hydrogen peroxide aqueous solution having a $H_2O_2$ content of 30 wt % in 229.7 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained.

(Ammoxidation of Propane)

Ammoxidation was carried out using the same process as in Example 1, but using the catalyst obtained in Comparative Example 5. The results after a reaction time of 5 hours are shown in Table 1, and the results after reaction times of 1200 and 3600 hours are shown in Table 2.

Comparative Example 6

Preparation of Catalyst

An oxide catalyst having a compositional formula as charged in represented by $Mo_1V_{0.32}Sb_{0.23}Nb_{0.07}Ti_{0.85}W_{0.05}O_n/41.3$ wt %-$SiO_2$ was prepared as follows. 314.3 g of ammonium heptamolybdate $((NH_4)_6Mo_7O_{24}.4H_2O)$, 66.2 g of ammonium metavanadate $(NH_4VO_3)$, 59.4 g of diantimony trioxide $(Sb_2O_3)$, and 120.0 g of titanium oxide were added to 1502 g of water, heating was carried out for 1 hour 30 minutes at 90° C. while stirring, and then cooling was carried out to approximately 70° C., thus obtaining a mixed liquid A-10. 649.7 g of a silica sol having a $SiO_2$ content of 29.3 wt % was added to the mixed liquid A-10 obtained. 65.6 g of a hydrogen peroxide aqueous solution having a $H_2O_2$ content of 30 wt % was further added, and stirring was continued for 1 hour at 52° C. In a separate vessel, 89.5 g of powdered silica was dispersed in 1342 g of water, and the mixture was stirred for at least 3 hours at room temperature so as to prepare a powdered silica dispersion. Next, a mixture of 28.4 g of a hydrogen peroxide aqueous solution having a $H_2O_2$ content of 30 wt % in 186.8 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained.

(Ammoxidation of Propane)

Ammoxidation was carried out using the same process as in Example 1, but using the catalyst obtained in Comparative Example 6. The results after a reaction time of 5 hours are shown in Table 1, and the results after reaction times of 1200 and 3600 hours are shown in Table 2.

Example 5

Preparation of Catalyst

An oxide catalyst having a compositional formula represented by $Mo_1V_{0.25}Sb_{0.28}Nb_{0.085}Mn_{0.002}Ce_{0.01}O_n/42$ wt %-$SiO_2$ was prepared as follows. 304.1 g of ammonium heptamolybdate $((NH_4)_6Mo_7O_{24}.4H_2O)$, 50.0 g of ammonium metavanadate $(NH_4VO_3)$, 70.1 g of diantimony trioxide $(Sb_2O_3)$, and 7.58 g of cerium nitrate $(Ce(NO_3)_3.6H_2O)$ were added to 1501 g of water, heating was carried out for 1 hour 30 minutes at 90° C. while stirring, and then cooling was carried out to approximately 70° C., thus obtaining a mixed liquid A-11. 621.2 g of a silica sol having a $SiO_2$ content of 29.3 wt % was added to the mixed liquid A-11 obtained. 81.5 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 16.1 g of oxalic acid and 33.0 g of a hydrogen peroxide aqueous solution having a $H_2O_2$ content of 30 wt % in 216.8 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained. Next, 1.38 g of manganese nitrate and 25 ml of 1 N nitric acid were added to 225 g of water, the pH being adjusted to 1, and the mixture was stirred so as to obtain a mixed liquid C-1. 50 g of the obtained catalyst was added to this mixed liquid C-1, and the mixture was stirred for 5 minutes, and then the whole vessel was put into a suction flask, and suction was carried out for 10 minutes. After recovering the catalyst through filtration, the catalyst was put into a drier and dried for 3 hours at 100° C., whereby a catalyst was obtained. The compositional formula of the catalyst was measured by X-ray fluorescence analysis (Rigaku RINT 1000, Cr tube, tube voltage 50 kV, tube current 50 mA).

(Ammoxidation of Propane)

Ammoxidation was carried out using the same process as in Example 1, but using the catalyst obtained in Example 5.

The results after a reaction time of 5 hours are shown in Table 3, and the results after reaction times of 1200 and 3600 hours are shown in Table 4.

Example 6

Preparation of Catalyst

An oxide catalyst having a compositional formula represented by $Mo_1V_{0.25}Sb_{0.28}Nb_{0.085}W_{0.005}Ce_{0.01}O_n/42M$ %-$SiO_2$ was prepared as follows. 304.1 g of ammonium heptamolybdate (($NH_4$)$_6Mo_7O_{24}$.4$H_2O$), 50.0 g of ammonium metavanadate ($NH_4VO_3$), 70.1 g of diantimony trioxide ($Sb_2O_3$), and 7.58 g of cerium nitrate ($Ce(NO_3)_3$.6$H_2O$) were added to 1501 g of water, heating was carried out for 1 hour 30 minutes at 90° C. while stirring, and then cooling was carried out to approximately 70° C., thus obtaining a mixed liquid A-12. 621.2 g of a silica sol having a $SiO_2$ content of 29.3 wt % was added to the mixed liquid A-12 obtained. 81.5 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 16.1 g of oxalic acid and 33.0 g of a hydrogen peroxide aqueous solution having a $H_2O_2$ content of 30 wt % in 216.8 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained. Next, 11.9 g of ammonium metatungstate having a $WO_3$ content of 50 wt % and 25 ml of 1 N nitric acid were added to 225 g of water, the pH being adjusted to 1, and the mixture was stirred so as to obtain a mixed liquid C-2. 50 g of the obtained catalyst was added to this mixed liquid C-2, and the mixture was stirred for 5 minutes, and then the whole vessel was put into a suction flask, and suction was carried out for 10 minutes. After recovering the catalyst through filtration, the catalyst was put into a drier and dried for 3 hours at 100° C., whereby a catalyst was obtained. The compositional formula of the catalyst was measured as in Example 5.
(Ammoxidation of Propane)

Ammoxidation was carried out using the same process as in Example 1, but using the catalyst obtained in Example 6. The results after a reaction time of 5 hours are shown in Table 3, and the results after reaction times of 1200 and 3600 hours are shown in Table 4.

Example 7

Preparation of Catalyst

An oxide catalyst having a compositional formula represented by $Mo_1V_{0.25}Sb_{0.28}Nb_{0.085}Mn_{0.0018}W_{0.005}Ce_{0.01}O_n/$ 42 wt %-$SiO_2$ was prepared as follows. 303.9 g of ammonium heptamolybdate (($NH_4$)$_6Mo_7O_{24}$.4$H_2O$), 50.0 g of ammonium metavanadate ($NH_4VO_3$), 70.1 g of diantimony trioxide ($Sb_2O_3$), and 7.57 g of cerium nitrate ($Ce(NO_3)_3$.6$H_2O$) were added to 1500 g of water, heating was carried out for 1 hour 30 minutes at 90° C. while stirring, and then cooling was carried out to approximately 70° C., thus obtaining a mixed liquid A-13. 621.2 g of a silica sol having a $SiO_2$ content of 29.3 wt % was added to the mixed liquid A-13 obtained. 81.4 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 16.1 g of oxalic acid and 33.6 g of a hydrogen peroxide aqueous solution having a $H_2O_2$ content of 30 wt % in 216.7 g of the niobium stock liquid prepared above, 0.88 g of manganese nitrate ($Mn(NO_3)_2$.6$H_2O$), and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained. Next, 8.06 g of ammonium metatungstate having a $WO_3$ content of 50 wt % and 25 ml of 1 N nitric acid were added to 225 g of water, the pH being adjusted to 1, and the mixture was stirred so as to obtain a mixed liquid C-3. 50 g of the obtained catalyst was added to this mixed liquid C-3, and the mixture was stirred for 5 minutes, and then the whole vessel was put into a suction flask, and suction was carried out for 10 minutes. After recovering the catalyst through filtration, the catalyst was put into a drier and dried for 3 hours at 100° C., whereby a catalyst was obtained. The compositional formula of the catalyst was measured as in Example 5.
(Ammoxidation of Propane)

Ammoxidation was carried out using the same process as in Example 1, but using the catalyst obtained in Example 7. The results after a reaction time of 5 hours are shown in Table 3, and the results after reaction times of 1200 and 3600 hours are shown in Table 4.

Example 8

Preparation of Catalyst

An oxide catalyst having a compositional formula represented by $Mo_1V_{0.25}Sb_{0.28}Nb_{0.085}Mn_{0.002}W_{0.025}Ce_{0.01}O_n/42$ wt %-$SiO_2$ was prepared as follows. 304.1 g of ammonium heptamolybdate (($NH_4$)$_6Mo_7O_{24}$.4$H_2O$), 50.0 g of ammonium metavanadate ($NH_4VO_3$), 70.1 g of diantimony trioxide ($Sb_2O_3$), and 7.58 g of cerium nitrate ($Ce(NO_3)_3$.6$H_2O$) were added to 1501 g of water, heating was carried out for 1 hour 30 minutes at 90° C. while stirring, and then cooling was carried out to approximately 70° C., thus obtaining a mixed liquid A-14. 621.2 g of a silica sol having a $SiO_2$ content of 29.3 wt % was added to the mixed liquid A-14 obtained. 81.5 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 16.1 g of oxalic acid and 33.0 g of a hydrogen peroxide aqueous solution having a $H_2O_2$ content of 30 wt % in 216.8 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained. Next, 0.72 g of manganese nitrate and 25 ml of 1 N nitric acid were added to 225 g of water, the pH being adjusted to 1, and the mixture was stirred so as to obtain a mixed liquid C-4. 50 g of the obtained catalyst was added to this mixed liquid C-4, and the mixture was stirred for 5 minutes, and then the whole vessel was put into a suction flask, and suction was carried out for 10 minutes. After recovering the catalyst through filtration, the catalyst was put into a drier and dried for 3 hours at 100° C., whereby a catalyst was obtained. The compositional formula of the catalyst was measured as in Example 5.

(Ammoxidation of Propane)

Ammoxidation was carried out using the same process as in Example 1, but using the catalyst obtained in Example 8. The results after a reaction time of 5 hours are shown in Table 3, and the results after reaction times of 1200 and 3600 hours are shown in Table 4.

Example 9

Preparation of Catalyst

An oxide catalyst having a compositional formula represented by $Mo_1V_{0.25}Sb_{0.28}Nb_{0.085}Mn_{0.001}W_{0.0006}Ce_{0.01}O_n$/42 wt %-$SiO_2$ was prepared as follows. 303.9 g of ammonium heptamolybdate ($(NH_4)_6Mo_7O_{24}\cdot 4H_2O$), 50.0 g of ammonium metavanadate ($NH_4VO_3$), 70.1 g of diantimony trioxide ($Sb_2O_3$), and 7.57 g of cerium nitrate ($Ce(NO_3)_3\cdot 6H_2O$) were added to 1500 g of water, heating was carried out for 1 hour 30 minutes at 90° C. while stirring, and then cooling was carried out to approximately 70° C., thus obtaining a mixed liquid A-15. 621.2 g of a silica sol having a $SiO_2$ content of 29.3 wt % was added to the mixed liquid A-15 obtained. 81.4 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 16.1 g of oxalic acid and 33.6 g of a hydrogen peroxide aqueous solution having a $H_2O_2$ content of 30 wt % in 216.7 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained. Next, 15.8 g of ammonium metatungstate having a $WO_3$ content of 50 wt %, 0.34 g of manganese nitrate, and 25 ml of 1 N nitric acid were added to 225 g of water, the pH being adjusted to 1, and the mixture was stirred so as to obtain a mixed liquid C-5. 50 g of the obtained catalyst was added to this mixed liquid C-5, and the mixture was stirred for 5 minutes, and then the whole vessel was put into a suction flask, and suction was carried out for 10 minutes. After recovering the catalyst through filtration, the catalyst was put into a drier and dried for 3 hours at 100° C., whereby a catalyst was obtained. The compositional formula of the catalyst was measured as in Example 5.

(Ammoxidation of Propane)

Ammoxidation was carried out using the same process as in Example 1, but using the catalyst obtained in Example 9. The results after a reaction time of 5 hours are shown in Table 3, and the results after reaction times of 1200 and 3600 hours are shown in Table 4.

Comparative Example 7

Preparation of Catalyst

An oxide catalyst having a compositional formula represented by $Mo_1V_{0.25}Sb_{0.28}Nb_{0.085}Ce_{0.01}O_n$/42 wt %-$SiO_2$ was prepared as follows. 303.9 g of ammonium heptamolybdate ($(NH_4)_6Mo_7O_{24}\cdot 4H_2O$), 50.0 g of ammonium metavanadate ($NH_4VO_3$), 70.1 g of diantimony trioxide ($Sb_2O_3$), and 7.57 g of cerium nitrate ($Ce(NO_3)_3\cdot 6H_2O$) were added to 1500 g of water, heating was carried out for 1 hour 30 minutes at 90° C. while stirring, and then cooling was carried out to approximately 70° C., thus obtaining a mixed liquid A-16. 621.2 g of a silica sol having a $SiO_2$ content of 29.3 wt % was added to the mixed liquid A-16 obtained. 81.4 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 16.1 g of oxalic acid and 33.6 g of a hydrogen peroxide aqueous solution having a $H_2O_2$ content of 30 wt % in 216.7 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained. Next, 50 g of the obtained catalyst was added to 250 g of water, and the mixture was stirred for 5 minutes, and then the whole vessel was put into a suction flask, and suction was carried out for 10 minutes. After recovering the catalyst through filtration, the catalyst was put into a drier and dried for 3 hours at 100° C., whereby a catalyst was obtained. The compositional formula of the catalyst was measured as in Example 5.

(Ammoxidation of Propane)

Ammoxidation was carried out using the same process as in Example 1, but using the catalyst obtained in Comparative Example 7. The results after a reaction time of 5 hours are shown in Table 3, and the results after reaction times of 1200 and 3600 hours are shown in Table 4.

Comparative Example 8

Preparation of Catalyst

An oxide catalyst having a compositional formula represented by $Mo_1V_{0.25}Sb_{0.28}Nb_{0.085}Ce_{0.01}O_n$/42 wt %-$SiO_2$ was prepared as follows. 303.9 g of ammonium heptamolybdate ($(NH_4)_6Mo_7O_{24}\cdot 4H_2O$), 50.0 g of ammonium metavanadate ($NH_4VO_3$), 70.1 g of diantimony trioxide ($Sb_2O_3$), and 7.57 g of cerium nitrate ($Ce(NO_3)_3\cdot 6H_2O$) were added to 1500 g of water, heating was carried out for 1 hour 30 minutes at 90° C. while stirring, and then cooling was carried out to approximately 70° C., thus obtaining a mixed liquid A-17. 621.2 g of a silica sol having a $SiO_2$ content of 29.3 wt % was added to the mixed liquid A-17 obtained. 81.4 g of a hydrogen peroxide aqueous solution having a $H_2O_2$ content of 30 wt % was further added, and stirring was continued for 1 hour at 52°

C. In a separate vessel, 91.0 g of powdered silica was dispersed in 1300 g of water, and the mixture was stirred for at least 3 hours at room temperature so as to prepare a powdered silica dispersion. Next, a mixture of 16.1 g of oxalic acid and 33.6 g of a hydrogen peroxide aqueous solution having a $H_2O_2$ content of 30 wt % in 216.7 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained. Next, 50 g of the obtained catalyst was added to a nitric acid aqueous solution that had been obtained by mixing together 25 g of a 1N nitric acid aqueous solution and 225 g of water, the pH being adjusted to 1, and the mixture was stirred for 5 minutes, and then the whole vessel was put into a suction flask, and suction was carried out for 10 minutes. After recovering the catalyst through filtration, the catalyst was put into a drier and dried for 3 hours at 100° C., whereby a catalyst was obtained. The compositional formula of the catalyst was measured as in Example 5.

(Ammoxidation of Propane)

Ammoxidation was carried out using the same process as in Example 1, but using the catalyst obtained in Comparative Example 8. The results after a reaction time of 5 hours are shown in Table 3, and the results after reaction times of 1200 and 3600 hours are shown in Table 4.

Comparative Example 9

Preparation of Catalyst

An oxide catalyst having a compositional formula represented by $Mo_1V_{0.25}Sb_{0.28}Nb_{0.085}Mn_{0.15}Ce_{0.01}O_n$/42 wt %-$SiO_2$ was prepared as follows. 303.9 g of ammonium heptamolybdate (($NH_4)_6Mo_7O_{24}.4H_2O$), 50.0 g of ammonium metavanadate ($NH_4VO_3$), 70.1 g of diantimony trioxide ($Sb_2O_3$), and 7.57 g of cerium nitrate ($Ce(NO_3)_3.6H_2O$) were added to 1500 g of water, heating was carried out for 1 hour 30 minutes at 90° C. while stirring, and then cooling was carried out to approximately 70° C., thus obtaining a mixed liquid A-18. 621.2 g of a silica sol having a $SiO_2$ content of 29.3 wt % was added to the mixed liquid A-18 obtained. 81.4 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 16.1 g of oxalic acid and 33.6 g of a hydrogen peroxide aqueous solution having a $H_2O_2$ content of 30 wt % in 216.7 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained. Next, 70.3 g of manganese nitrate and 25 ml of 1 N nitric acid were added to 155 g of water, the pH being adjusted to 1, and the mixture was stirred so as to obtain a mixed liquid C-6. 50 g of the obtained catalyst was added to this mixed liquid C-6, and the mixture was stirred for 5 minutes, and then the whole vessel was put into a suction flask, and suction was carried out for 10 minutes. The catalyst was put into a drier and dried for 3 hours at 100° C., whereby a catalyst was obtained. The compositional formula of the catalyst was measured as in Example 5.

(Ammoxidation of Propane)

Ammoxidation was carried out using the same process as in Example 1, but using the catalyst obtained in Comparative Example 9. The results after a reaction time of 5 hours are shown in Table 3, and the results after reaction times of 1200 and 3600 hours are shown in Table 4.

Comparative Example 10

Preparation of Catalyst

An oxide catalyst having a compositional formula represented by $Mo_1V_{0.25}Sb_{0.28}Nb_{0.085}W_{0.18}Ce_{0.01}O_n$/42 wt %-$SiO_2$ was prepared as follows. 255.7 g of ammonium heptamolybdate (($NH_4)_6Mo_7O_{24}.4H_2O$), 42.1 g of ammonium metavanadate ($NH_4VO_3$), 59.0 g of diantimony trioxide ($Sb_2O_3$), and 6.37 g of cerium nitrate ($Ce(NO_3)_3.6H_2O$) were added to 1262 g of water, heating was carried out for 1 hour 30 minutes at 90° C. while stirring, and then cooling was carried out to approximately 70° C., thus obtaining a mixed liquid A-19. 621.2 g of a silica sol having a $SiO_2$ content of 29.3 wt % was added to the mixed liquid A-19 obtained. 68.5 g of a hydrogen peroxide aqueous solution having a $H_2O_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 13.5 g of oxalic acid and 27.7 g of a hydrogen peroxide aqueous solution having a $H_2O_2$ content of 30 wt % in 182.3 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained. Next, 120 g of ammonium metatungstate having a $WO_3$ content of 50 wt % and 25 ml of 1 N nitric acid were added to 225 g of water, the pH being adjusted to 1, and the mixture was stirred so as to obtain a mixed liquid C-7. 50 g of the obtained catalyst was added to this mixed liquid C-7, and the mixture was stirred for 5 minutes, and then the whole vessel was put into a suction flask, and suction was carried out for 10 minutes. The catalyst was put into a drier and dried for 3 hours at 100° C., whereby a catalyst was obtained. The compositional formula of the catalyst was measured as in Example 5.

(Ammoxidation of Propane)

Ammoxidation was carried out using the same process as in Example 1, but using the catalyst obtained in Comparative Example 10. The results after a reaction time of 5 hours are shown in Table 3, and the results after reaction times of 1200 and 3600 hours are shown in Table 4.

Comparative Example 11

Preparation of Catalyst

An oxide catalyst having a compositional formula represented by $Mo_1V_{0.25}Sb_{0.28}Nb_{0.085}Mn_{0.07}W_{0.08}Ce_{0.01}O_n$/42 wt %-SiO$_2$ was prepared as follows. 274.8 g of ammonium heptamolybdate ((NH$_4$)$_6$Mo$_7$O$_{24}$.4H$_2$O), 45.2 g of ammonium metavanadate (NH$_4$VO$_3$), 63.4 g of diantimony trioxide (Sb$_2$O$_3$), and 6.85 g of cerium nitrate (Ce(NO$_3$)$_3$.6H$_2$O) were added to 1360 g of water, heating was carried out for 1 hour 30 minutes at 90° C. while stirring, and then cooling was carried out to approximately 70° C., thus obtaining a mixed liquid A-20. 621.2 g of a silica sol having a SiO$_2$ content of 29.3 wt % was added to the mixed liquid A-20 obtained. 73.6 g of a hydrogen peroxide aqueous solution having a H$_2$O$_2$ content of 30 wt % was further added, and stirring was continued for 1 hour at 52° C. In a separate vessel, 91.0 g of powdered silica was dispersed in 1300 g of water, and the mixture was stirred for at least 3 hours at room temperature so as to prepare a powdered silica dispersion. Next, a mixture of 14.5 g of oxalic acid and 29.8 g of a hydrogen peroxide aqueous solution having a H$_2$O$_2$ content of 30 wt % in 195.9 g of the niobium stock liquid prepared above, and the powdered silica dispersion were added, thus obtaining a raw material mixture. The raw material mixture obtained was dried using a centrifugal spray drier, thus obtaining a microspherical dry powder. The inlet temperature of the drier was 210° C., and the outlet temperature was 120° C. 500 g of the dry powder obtained was packed into a 3-inch-diameter SUS kiln, and was calcined for 2 hours at 640° C. under a 1000 Ncc/min nitrogen gas stream, whereby a catalyst was obtained. Next, 57.3 g of ammonium metatungstate having a WO$_3$ content of 50 wt %, 31.1 g of manganese nitrate, and 25 ml of 1 N nitric acid were added to 137 g of water, the pH being adjusted to 1, and the mixture was stirred so as to obtain a mixed liquid C-8. 50 g of the obtained catalyst was added to this mixed liquid C-8, and the mixture was stirred for 5 minutes, and then the whole vessel was put into a suction flask, and suction was carried out for 10 minutes. The catalyst was put into a drier and dried for 3 hours at 100° C., whereby a catalyst was obtained. The compositional formula of the catalyst was measured as in Example 5.

(Ammoxidation of Propane)

Ammoxidation was carried out using the same process as in Example 1, but using the catalyst obtained in Comparative Example 11. The results after a reaction time of 5 hours are shown in Table 3, and the results after reaction times of 1200 and 3600 hours are shown in Table 4.

TABLE 1

| | Catalytic Composition | Propane Conversion [%] | Acrylonitrile Yield [%] |
|---|---|---|---|
| Example 1 | Mo$_1$V$_{0.25}$Nb$_{0.085}$Sb$_{0.28}$Mn$_{0.0025}$W$_{0.01}$Ce$_{0.01}$O$_n$/ 42 wt %-SiO$_2$ | 89.0 | 54.8 |
| Example 2 | Mo$_1$V$_{0.25}$Nb$_{0.085}$Sb$_{0.28}$Mn$_{0.003}$Ce$_{0.01}$O$_n$/ 42 wt %-SiO$_2$ | 88.9 | 53.6 |
| Example 3 | Mo$_1$V$_{0.25}$Nb$_{0.085}$Sb$_{0.28}$W$_{0.03}$Ce$_{0.01}$O$_n$/ 42 wt %-SiO$_{2n}$ | 89.1 | 53.8 |
| Example 4 | Mo$_1$V$_{0.25}$Nb$_{0.085}$Sb$_{0.28}$Mn$_{0.004}$W$_{0.01}$O$_n$/ 42 wt %-SiO$_2$ | 88.5 | 54.0 |
| Comparative Example 1 | Mo$_1$V$_{0.25}$Nb$_{0.085}$Sb$_{0.28}$Ce$_{0.01}$O$_n$/ 42 wt %-SiO$_2$ | 87.0 | 52.4 |
| Comparative Example 2 | Mo$_1$V$_{0.25}$Nb$_{0.085}$Sb$_{0.28}$Mn$_{0.2}$Ce$_{0.01}$O$_n$/ 42 wt %-SiO$_2$ | 85.9 | 49.9 |
| Comparative Example 3 | Mo$_1$V$_{0.25}$Nb$_{0.085}$Sb$_{0.28}$W$_{0.2}$Ce$_{0.01}$O$_n$/ 42 wt %-SiO$_2$ | 78.1 | 49.2 |
| Comparative Example 4 | Mo$_1$V$_{0.25}$Nb$_{0.085}$Sb$_{0.28}$Mn$_{0.08}$W$_{0.08}$Ce$_{0.01}$O$_n$/ 42 wt %-SiO$_2$ | 76.3 | 44.9 |
| Comparative Example 5 | Mo$_1$V$_{0.21}$Nb$_{0.09}$Sb$_{0.25}$Ce$_{0.005}$O$_n$/ 45 wt %-SiO$_2$ | 88.1 | 53.0 |
| Comparative Example 6 | Mo$_1$V$_{0.32}$Nb$_{0.07}$Sb$_{0.23}$Ti$_{0.85}$W$_{0.05}$O$_n$/ 41.3 wt %-SiO$_2$ | 87.8 | 52.3 |

TABLE 2

| | Catalytic Composition | Acrylonitrile yield after 1200 hours [%] | Acrylonitrile yield after 3600 hours [%] |
|---|---|---|---|
| Example 1 | Mo$_1$V$_{0.25}$Nb$_{0.085}$Sb$_{0.28}$Mn$_{0.0025}$W$_{0.01}$Ce$_{0.01}$O$_n$/ 42 wt %-SiO$_2$ | 54.6 | 54.5 |
| Example 2 | Mo$_1$V$_{0.25}$Nb$_{0.085}$Sb$_{0.28}$Mn$_{0.003}$Ce$_{0.01}$O$_n$/ 42 wt %-SiO$_2$ | 53.3 | 53.2 |
| Example 3 | Mo$_1$V$_{0.25}$Nb$_{0.085}$Sb$_{0.28}$W$_{0.03}$Ce$_{0.01}$O$_n$/ 42 wt %-SiO$_{2n}$ | 53.4 | 53.2 |
| Example 4 | Mo$_1$V$_{0.25}$Nb$_{0.085}$Sb$_{0.28}$Mn$_{0.004}$W$_{0.01}$O$_n$/ 42 wt %-SiO$_2$ | 53.3 | 52.7 |
| Comparative Example 1 | Mo$_1$V$_{0.25}$Nb$_{0.085}$Sb$_{0.28}$Ce$_{0.01}$O$_n$/ 42 wt %-SiO$_2$ | 49.8 | 48.4 |
| Comparative Example 2 | Mo$_1$V$_{0.25}$Nb$_{0.085}$Sb$_{0.28}$Mn$_{0.2}$Ce$_{0.01}$O$_n$/ 42 wt %-SiO$_2$ | 48.9 | 47.3 |
| Comparative Example 3 | Mo$_1$V$_{0.25}$Nb$_{0.085}$Sb$_{0.28}$W$_{0.2}$Ce$_{0.01}$O$_n$/ 42 wt %-SiO$_2$ | 46.7 | 42.2 |
| Comparative Example 4 | Mo$_1$V$_{0.25}$Nb$_{0.085}$Sb$_{0.28}$Mn$_{0.08}$W$_{0.08}$Ce$_{0.01}$O$_n$/ 42 wt %-SiO$_2$ | 42.0 | 37.4 |
| Comparative Example 5 | Mo$_1$V$_{0.21}$Nb$_{0.09}$Sb$_{0.25}$Ce$_{0.005}$O$_n$/ 45 wt %-SiO$_2$ | 52.0 | 51.5 |
| Comparative Example 6 | b$_0$. Mo$_1$V$_{0.32}$Nb$_{0.07}$Sb$_{0.23}$Ti$_{0.85}$W$_{0.05}$O$_n$ wt %-SiO$_2$ | 51.7 | 50.5 |

TABLE 3

| | Catalytic Composition | Propane Conversion [%] | Acrylonitrile Yield [%] |
|---|---|---|---|
| Example 5 | $Mo_1V_{0.25}Nb_{0.085}Sb_{0.28}Mn_{0.002}Ce_{0.01}O_n$/42 wt%-$SiO_2$ | 88.7 | 53.8 |
| Example 6 | $Mo_1V_{0.25}Nb_{0.085}Sb_{0.28}W_{0.005}Ce_{0.01}O_n$/42 wt%-$SiO_2$ | 88.9 | 54.6 |
| Example 7 | $Mo_1V_{0.25}Nb_{0.085}Sb_{0.28}Mn_{0.0018}W_{0.005}Ce_{0.01}O_n$/42 wt%-$SiO_{2n}$ | 89.0 | 55.2 |
| Example 8 | $Mo_1V_{0.25}Nb_{0.085}Sb_{0.28}Mn_{0.002}W_{0.025}O_n$/42 wt%-$SiO_2$ | 87.9 | 54.2 |
| Example 9 | $Mo_1V_{0.25}Nb_{0.085}Sb_{0.30}Mn_{0.001}W_{0.006}Ce_{0.01}O_n$/42 wt%-$SiO_2$ | 88.1 | 53.9 |
| Comparative Example 7 | $Mo_1V_{0.25}Nb_{0.085}Sb_{0.28}Ce_{0.01}O_n$/42 wt%-$SiO_2$ | 85.0 | 49.5 |
| Comparative Example 8 | $Mo_1V_{0.25}Nb_{0.085}Sb_{0.28}Ce_{0.01}O_n$/42 wt%-$SiO_2$ | 85.5 | 50.7 |
| Comparative Example 9 | $Mo_1V_{0.25}Nb_{0.085}Sb_{0.28}Mn_{0.15}Ce_{0.01}O_n$/42 wt%-$SiO_2$ | 77.3 | 47.3 |
| Comparative Example 10 | $Mo_1V_{0.25}Nb_{0.085}Sb_{0.28}W_{0.18}Ce_{0.01}O_n$/42 wt%-$SiO_2$ | 75.5 | 48.5 |
| Comparative Example 11 | $Mo_1V_{0.21}Nb_{0.09}Sb_{0.25}Mn_{0.07}W_{0.08}Ce_{0.005}O_n$/42 wt%-$SiO_2$ | 71.5 | 46.4 |

TABLE 4

| | Catalytic Composition | Acrylonitrile yield after 1200 hours [%] | Acrylonitrile yield after 3600 hours [%] |
|---|---|---|---|
| Example 5 | $Mo_1V_{0.25}Nb_{0.085}Sb_{0.28}Mn_{0.002}Ce_{0.01}O_n$/42 wt%-$SiO_2$ | 53.8 | 53.5 |
| Example 6 | $Mo_1V_{0.25}Nb_{0.085}Sb_{0.28}W_{0.005}Ce_{0.01}O_n$/42 wt%-$SiO_2$ | 54.6 | 54.4 |
| Example 7 | $Mo_1V_{0.25}Nb_{0.085}Sb_{0.28}Mn_{0.0018}W_{0.005}Ce_{0.01}O_n$/42 wt%-$SiO_{2n}$ | 55.2 | 55.1 |
| Example 8 | $Mo_1V_{0.25}Nb_{0.085}Sb_{0.28}Mn_{0.002}W_{0.025}O_n$/42 wt%-$SiO_2$ | 54.2 | 54.0 |
| Example 9 | $Mo_1V_{0.25}Nb_{0.085}Sb_{0.30}Mn_{0.001}W_{0.006}Ce_{0.01}O_n$/42 wt%-$SiO_2$ | 53.9 | 53.6 |
| Comparative Example 7 | $Mo_1V_{0.25}Nb_{0.085}Sb_{0.28}Ce_{0.01}O_n$/42 wt%-$SiO_2$ | 49.5 | 48.8 |
| Comparative Example 8 | $Mo_1V_{0.25}Nb_{0.085}Sb_{0.28}Ce_{0.01}O_n$/42 wt%-$SiO_2$ | 50.7 | 49.8 |
| Comparative Example 9 | $Mo_1V_{0.25}Nb_{0.085}Sb_{0.28}Mn_{0.15}Ce_{0.01}O_n$/42 wt%-$SiO_2$ | 47.3 | 45.1 |
| Comparative Example 10 | $Mo_1V_{0.25}Nb_{0.085}Sb_{0.28}W_{0.18}Ce_{0.01}O_n$/42 wt%-$SiO_2$ | 48.5 | 46.9 |
| Comparative Example 11 | $Mo_1V_{0.21}Nb_{0.09}Sb_{0.25}Mn_{0.07}W_{0.08}Ce_{0.005}O_n$/42 wt%-$SiO_2$ | 46.4 | 41.2 |

INDUSTRIAL APPLICABILITY

The oxide catalyst according to the present invention can be suitably used in the vapor-phase catalytic oxidation or the vapor-phase catalytic ammoxidation of propane, isobutane or the like.

We claim:

1. An oxide catalyst for use in a vapor-phase catalytic oxidation or a vapor-phase catalytic ammoxidation of propane or isobutane, the oxide catalyst represented by following compositional formula (1):

$$Mo_1V_aSb_bNb_cMn_dW_eY_fO_n \qquad (1)$$

wherein Y represents at least one element selected from alkaline earth metals and rare earth metals;
    a, b, c, d, e, f, and n each represents an atomic ratio based on one atom of Mo;
    $0.1 \leq a \leq 1$, $0.01 \leq b \leq 1$, $0.01 \leq c \leq 1$, $0 \leq d \leq 0.1$, $0 \leq e \leq 0.1$, $0 < (d+e) \leq 0.1$, $0 \leq f \leq 1$; and
    n is a number determined by valencies of the constituent metals.

2. The oxide catalyst according to claim 1, wherein in the compositional formula (1), e=0, and $0<d \leq 0.08$.

3. The oxide catalyst according to claim 1, wherein in the compositional formula (1), d=0, and $0<e \leq 0.08$.

4. The oxide catalyst according to claim 1, wherein in the compositional formula (1), $0<d$, $0 \leq e$, and $(d+e) \leq 0.08$.

5. The oxide catalyst according to any one of claims 1 to 4, wherein in the compositional formula (1), Y is cerium, and f>0.

6. The oxide catalyst according to any one of claims 1 to 5, wherein the oxide catalyst is supported on silica, wherein a weight ratio of the silica is from 10 to 80 wt% in terms of $SiO_2$ based on the total weight of the silica and the oxide catalyst.

7. A process for producing the oxide catalyst according to any one of claims 1 to 6, comprising;
    drying a mixture containing Mo, V, Sb, Nb, and Y (wherein Y represents at least one element selected from alkaline earth metals and rare earth metals), and Mn and/or W.

8. A process for producing the oxide catalyst according to any one of claims 1 to 6, comprising;
    mixing together a niobium-containing liquid having a dicarboxylic acid/niobium compound molar ratio of from 1 to 5, and a solution containing Mo, V and Sb.

9. A process for producing the oxide catalyst according to any one of claims 1 to 6, comprising the steps of;
    obtaining a catalyst precursor containing Mo, V, Sb and Nb; and
    immersing the catalyst precursor in a solution containing Mn and/or W.

10. The process for producing the oxide catalyst according to claim 9, wherein the catalyst precursor comprises Mn and/or W.

11. The process for producing the oxide catalyst according to claim 9 or 10, wherein the catalyst precursor comprises Y (wherein Y represents at least one element selected from alkaline earth metals and rare earth metals).

12. The process for producing the oxide catalyst according to claim 9 or 10, wherein the solution containing Mn and/or W has a pH of not more than 7.

13. A process for producing an unsaturated acid or unsaturated nitrile by subjecting propane or isobutane to a vapor-phase catalytic oxidation or a vapor-phase catalytic ammoxidation, the process comprising bringing the propane or isobutane into contact with the oxide catalyst according to any one of claims 1 to 6.

\* \* \* \* \*